(12) United States Patent
Yoshima et al.

(10) Patent No.: US 6,485,936 B1
(45) Date of Patent: Nov. 26, 2002

(54) HEAT SHOCK TRANSCRIPTION FACTOR-BINDING PROTEIN

(75) Inventors: Tadahiko Yoshima, Osaka; Hideki Yanagi, Takarazuka; Takashi Yura, Kyoto, all of (JP)

(73) Assignee: HSP Research Institute, Inc., Osaka (JP)

( * ) Notice: Subject to any disclaimer, the term of this patent is extended or adjusted under 35 U.S.C. 154(b) by 0 days.

(21) Appl. No.: 09/582,441

(22) PCT Filed: Dec. 18, 1998

(86) PCT No.: PCT/JP98/05728

§ 371 (c)(1),
(2), (4) Date: Aug. 18, 2000

(87) PCT Pub. No.: WO99/33975

PCT Pub. Date: Jul. 8, 1999

(30) Foreign Application Priority Data

Dec. 26, 1997 (JP) .............................................. 9-360640

(51) Int. Cl.[7] ........................ C12N 15/00; C12P 21/06; C07H 21/04; C07K 14/00
(52) U.S. Cl. ................... 435/69.1; 435/320.1; 435/325; 435/387.1; 536/23.1; 536/23.5; 536/24.5; 530/350
(58) Field of Search ............................ 435/6, 70.1, 69.1, 435/325, 320.1; 536/23.1, 24.3, 24.33, 24.5; 530/387.1, 350, 300

(56) References Cited

U.S. PATENT DOCUMENTS 5,194,596 A * 3/1993 Tischer et al. ............... 530/399
5,350,836 A * 9/1994 Kopchick et al. ............ 530/399

OTHER PUBLICATIONS

C.C. Pilbeam et al., Comparison of the Effects of Various Lengths of Synthetic Human Parathyroid Hormaone—Related Pepetide (hPTHrP) of Malignancy on Bone Resorption and Formation in Organ Culture, Bone, 14, (1993) pp. 717–720.*

Slobodan Vukicevic et al., Induction of nephrogenic mesenchyme by osteogenic protein 1 (bone morphogenetic protein 7), Proc. Natl. Sci., vol. 93, pp. 9021–9026.*

Laura E. Benjamin et al., A plasticity window for blood vessel remodeling is defined by pericyte coverage of the preformed endothelial network and is regulated by PDGF–B and VEGF, Development 125, pp. 1591–1598.*

Go hunting in sequence databases but watch out for the traps, TIG, Oct. 1996, vol. 12, No. 10, pp. 425–427.*

Errors in genome annotation, TIG, Apr. 1999, vol. 15, No. 4, pp. 132–133.*

(List continued on next page.)

Primary Examiner—John L. LeGuyader
Assistant Examiner—M Schmidt
(74) Attorney, Agent, or Firm—Birch, Stewart, Kolasch & Birch, LLP.

(57) ABSTRACT

To provide a heat shock transcription factor (HSF) 2 binding factor, which can be involved in the transcriptional regulation of HSP70.2 playing an essential role in spermatogenesis; a DNA encoding the binding factor; an expression vector carrying the DNA; a transformant harboring the expression vector; a process for preparing a recombinant protein comprising the step of culturing the transformant; an antibody or a fragment thereof capable of specifically binding to the binding factor; an antisense DNA or antisense RNA complementary to the DNA; and an oligonudeotide probe or primer capable of specifically hybridizing to the DNA.

7 Claims, 10 Drawing Sheets

OTHER PUBLICATIONS

Temple F. Smith et al., The challenges of genome sequence annotation or "The devil in the details", Nature Biotechnology, vol. 15, Nov. 1997, pp. 1222–1223.*

Protein annotation detective work for function prediction, TIG, Jun. 1998, vol. 14, No. 6, pp. 248–250.*

Jeffrey Skolick et al., From genes to protein structure and function: novel applications of computational approaches in the genomic era, Trends in Biotech, 18(1), pp. 34–39.*

Peer Bork, Power and Pitfalls in Sequence Analysis: The 70% Hurdle, Genome Research, pp. 398–400.*

J. Thomas Ngo et al., Computational Complexity, Protein Structure Prediction and the Levinthal Paradox, pp. 491–495.*

James A. Wells, Addivity of Mutational Effects in Proteins, Biochemistry, vol. 29, No. 37, pp. 8509–8517.*

Sistonen, Lea et al., Mol. and Cell. Bio., vol. 12, No. 9 (1992) pp. 4104–4111.

Sarge, Kevin D. et al., Bio. of Repro., vol. 50 (1994) pp. 1334–1343.

Murphy, Shawn P. et al., Mol. And Cell. Bio., vol. 14, No. 8 (1994) pp. 5309–5317.

Rallu, M. et al., Proc. Natl. Acad. Sci USA, vol. 94 (1997) pp. 2392–2397.

Sarge, K. D. et al., Cell. Mol. Life. Sci., vol. 53 (1997) pp. 191–197.

Allen, Randy L. et al., Mol. And Cell. Bio., vol. 8, No. 2 (1988) pp. 828–832.

Zakeri, Zahra F. et al., Mol. And Cell. Bio., vol. 8, No. 7 (1988) pp. 2925–2932.

Dix, David J. et al., Proc. Natl. Acad. Sci. USA, vol. 93 (1996) pp. 3264–3268.

Fields, Stanley, Nature, vol. 340 (1989) pp. 245–246.

Fields, Stanley, TIG, vol. 10, No. 8 (1994) pp. 286–292.

Mendelsohn, Andrew R. et al., Current Opinion in Biotech., vol. 5 (1994) pp. 482–486.

Takahiko Yoshima et al., "Novel testis–specific protein that interacts with heat shock factor 2", Gene (Jul. 3, 1998), vol. 214, pp. 139–146.

Kevin D. Sarge et al., "Expression of heat shock factor 2 in mouse testis" Biology of Reproduction (1994), vol. 50, pp. 1334–1343.

* cited by examiner

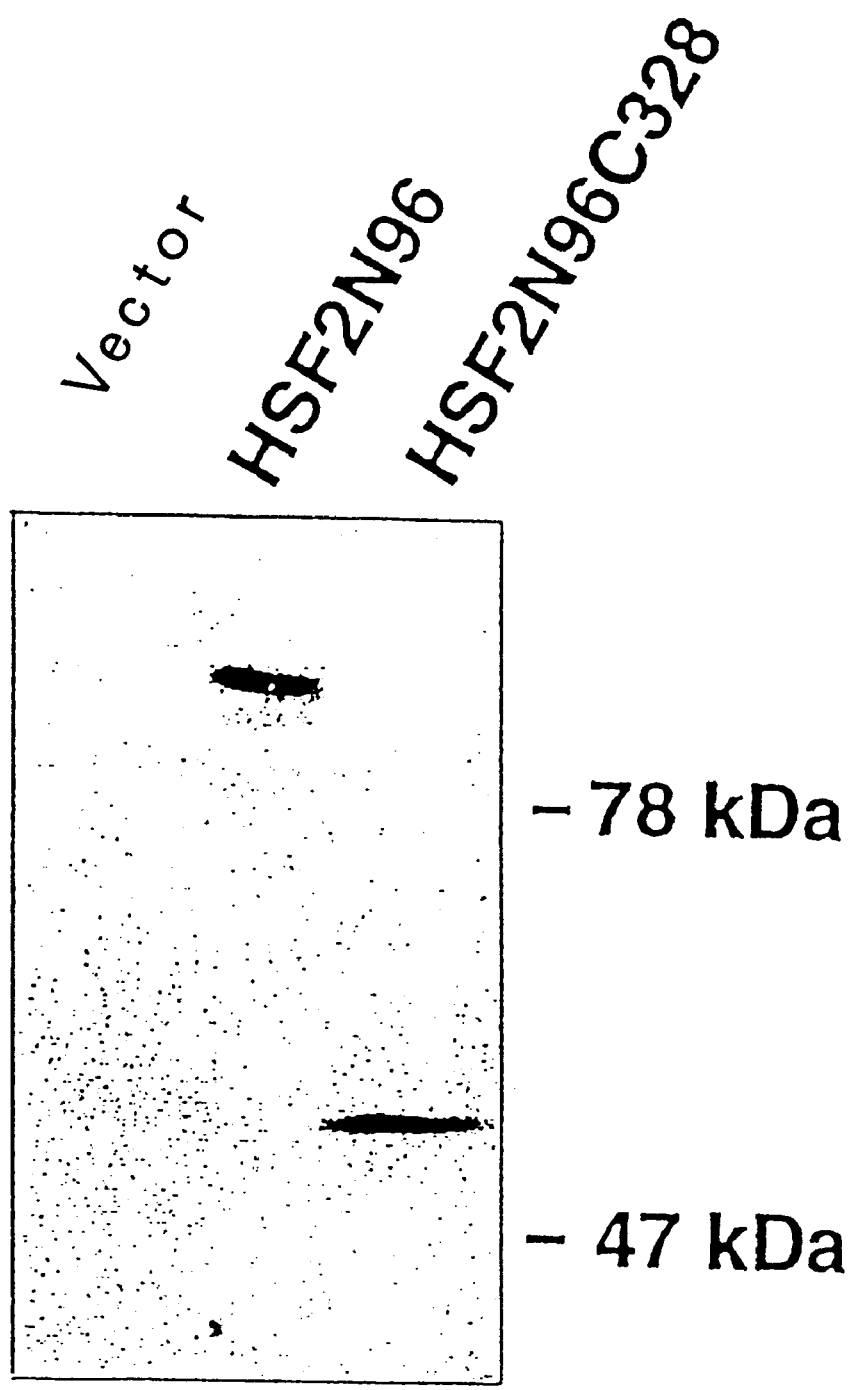
F I G. 2

FIG. 3

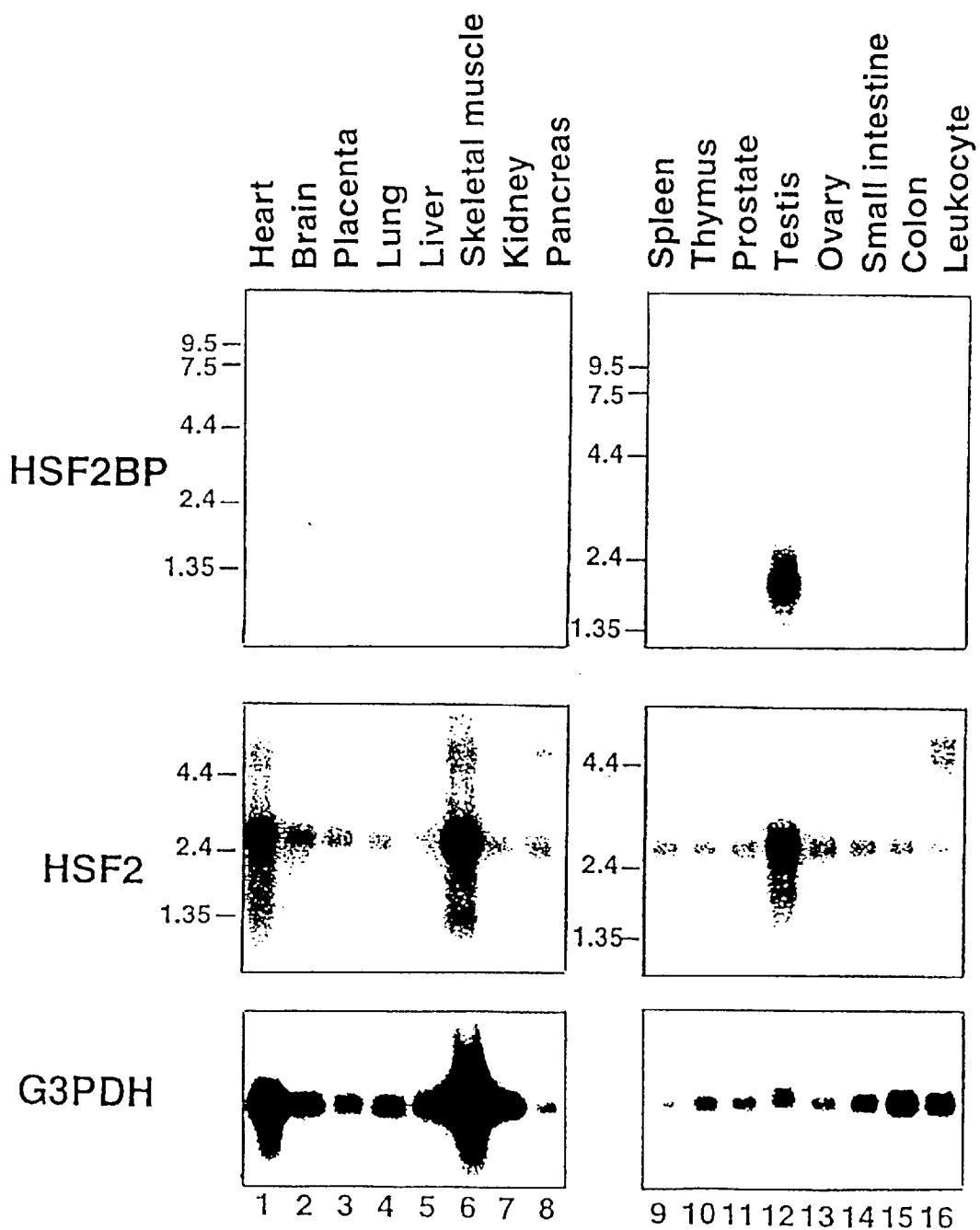
F I G. 5

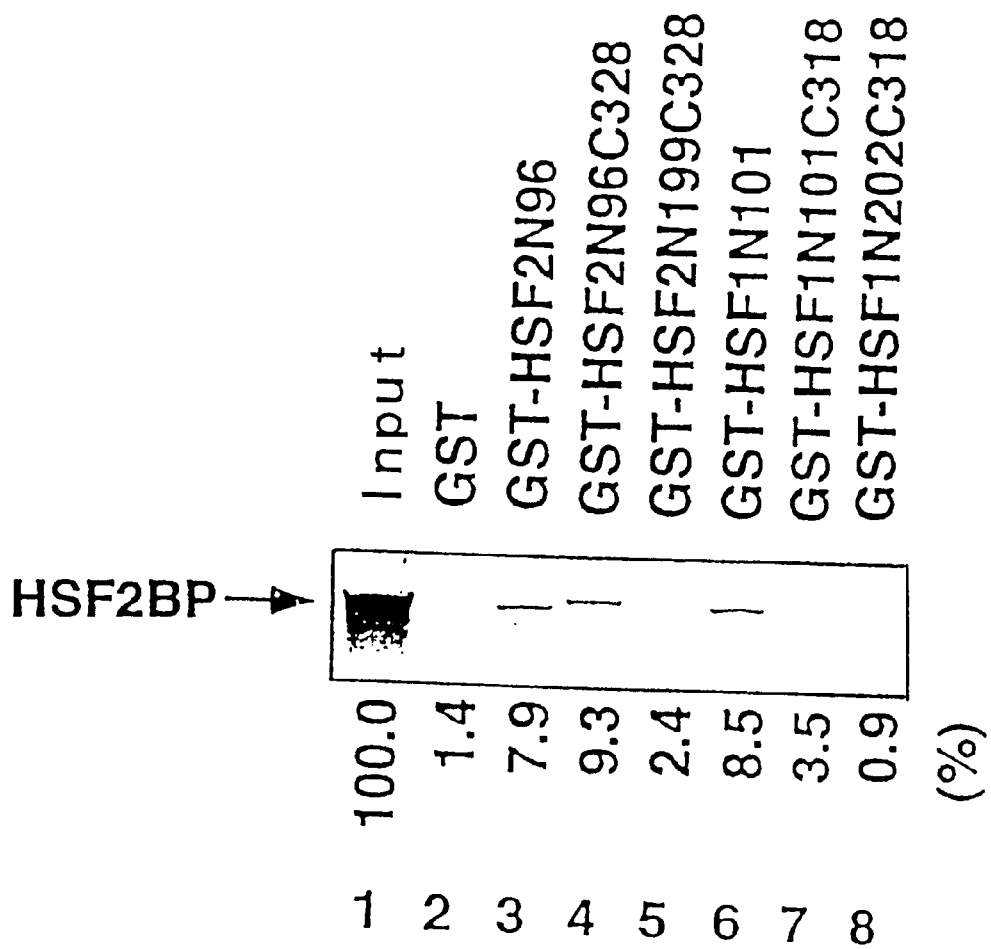
F I G. 6

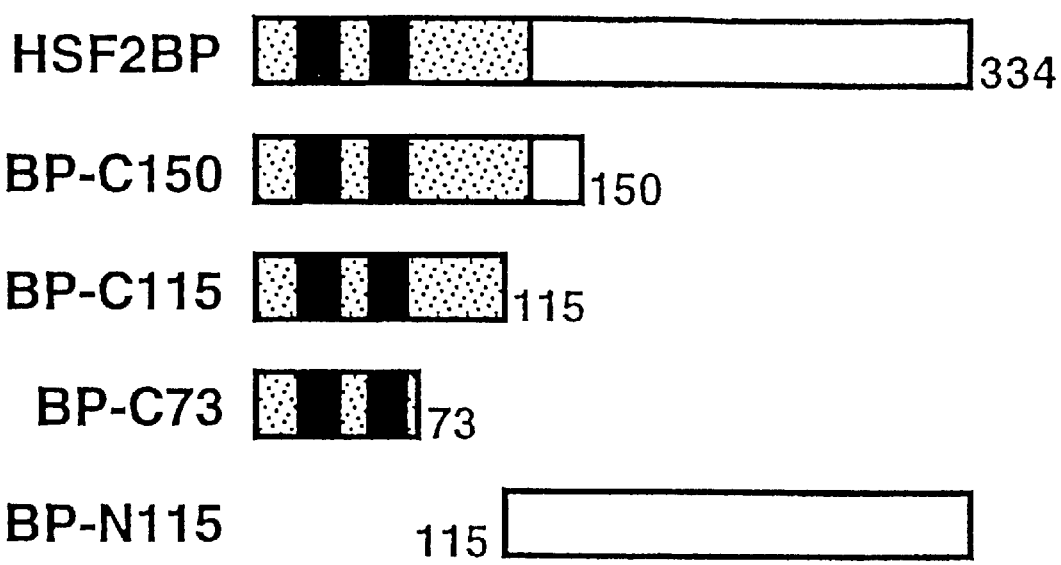
F I G. 7

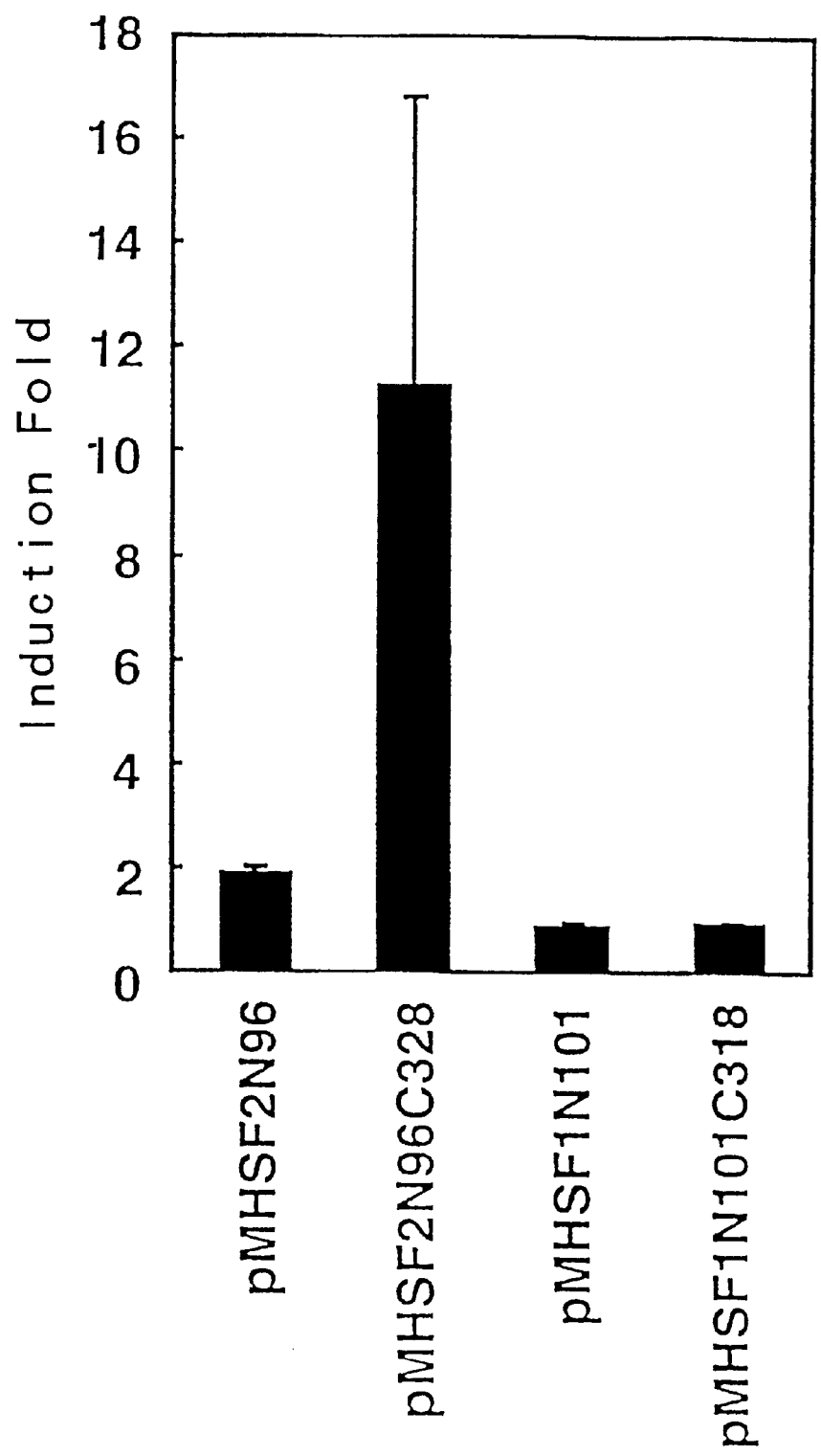
F I G. 10

SEQUENCE LISTING

<160> NUMBER OF SEQ ID NOS: 2

<210> SEQ ID NO 1
<211> LENGTH: 334
<212> TYPE: PRT
<213> ORGANISM: Homo sapien

<400> SEQUENCE: 1

```
Met Gly Glu Ala Gly Ala Ala Glu Glu Ala Cys Arg His Met Gly Thr
1               5                   10                  15

Lys Glu Glu Phe Val Lys Val Arg Lys Lys Asp Leu Glu Arg Leu Thr
            20                  25                  30

Thr Glu Val Met Gln Ile Arg Asp Phe Leu Pro Arg Ile Leu Asn Gly
        35                  40                  45

Glu Val Leu Glu Ser Phe Gln Lys Leu Lys Ile Val Glu Lys Asn Leu
    50                  55                  60

Glu Arg Lys Glu Gln Glu Leu Glu Gln Leu Lys Met Asp Cys Glu His
65                  70                  75                  80

Phe Lys Ala Arg Leu Glu Thr Val Gln Ala Asp Asn Ile Arg Glu Lys
                85                  90                  95

Lys Glu Lys Leu Ala Leu Arg Gln Gln Leu Asn Glu Ala Lys Gln Gln
            100                 105                 110

Leu Leu Gln Gln Ala Glu Tyr Cys Thr Glu Met Gly Ala Ala Ala Cys
        115                 120                 125

Thr Leu Leu Trp Gly Val Ser Ser Glu Glu Val Val Lys Ala Ile
    130                 135                 140

Leu Gly Gly Asp Lys Ala Leu Lys Phe Phe Ser Ile Thr Gly Gln Thr
145                 150                 155                 160

Met Glu Ser Phe Val Lys Ser Leu Asp Gly Asp Val Gln Glu Leu Asp
                165                 170                 175

Ser Asp Glu Ser Gln Phe Val Phe Ala Leu Ala Gly Ile Val Thr Asn
            180                 185                 190

Val Ala Ala Ile Ala Cys Gly Arg Glu Phe Leu Val Asn Ser Ser Arg
        195                 200                 205

Val Leu Leu Asp Thr Ile Leu Gln Leu Leu Gly Asp Leu Lys Pro Gly
    210                 215                 220

Gln Cys Thr Lys Leu Lys Val Leu Met Leu Met Ser Leu Tyr Asn Val
225                 230                 235                 240

Ser Ile Asn Leu Lys Gly Leu Lys Tyr Ile Ser Glu Ser Pro Gly Phe
                245                 250                 255

Ile Pro Leu Leu Trp Trp Leu Leu Ser Asp Pro Asp Ala Glu Val Cys
            260                 265                 270

Leu His Val Leu Arg Leu Val Gln Ser Val Val Leu Glu Pro Glu Val
        275                 280                 285

Phe Ser Lys Ser Ala Ser Glu Phe Arg Ser Ser Leu Pro Leu Gln Arg
    290                 295                 300
```

-continued

Ile Leu Ala Met Ser Lys Ser Arg Asn Pro A rg Leu Gln Thr Ala Ala
305 310 315 320

Gln Glu Leu Leu Glu Asp Leu Arg Thr Leu G lu His Asn Val
325 330

<210> SEQ ID NO 2
<211> LENGTH: 1916
<212> TYPE: DNA
<213> ORGANISM: Homo sapien

<400> SEQUENCE: 2

| | | | | | |
|---|---|---|---|---|---|
| ggagtgagcg | cggcagtggc | cctggcagct | ggcggagcgg | cccagcccgt g | tgcacgtgg 60 |
| cgccggcgct | gcctttcggt | tgccaaaatt | caggctgtag | acggcgagat a | acaagttta 120 |
| aaaccccggc | taagccagaa | gagccaaaga | gggacctcgc | caaggccact c | ctcgctctc 180 |
| taggccgaga | atactgcgca | aattctggga | ggtttgggcc | tggcggctct c | cgttcccga 240 |
| cccccggcgt | ggattcgttc | ccgcgctttc | tggcgtgagg | ggtcagaggg c | gcgccgacg 300 |
| ctcaggcgaa | cggagcggag | gcggcagcgg | ccatgggcga | agcgggcgcc g | ctgaggagg 360 |
| cctgccggca | catgggaact | aaagaggaat | ttgttaaagt | cagaaagaag g | atctggaac 420 |
| ggctgacaac | tgaagtgatg | caaatacggg | acttcttacc | agaatacta a | atggggagg 480 |
| tgctggagag | cttccagaaa | ttaaagattg | tagaaaaaaa | cctggaaagg a | aagagcaag 540 |
| aattagcagc | agctgaaaatg | gattgtgagc | actttaaagc | ccgcctggaa a | ccgtgcagg 600 |
| ccgacaacat | aagagagaag | aaggagaaac | tggctcttcg | acagcagttg a | atgaagcga 660 |
| agcagcaact | cctgcagcag | gcagagtatt | gtacagaaat | gggagcagca g | cgtgtaccc 720 |
| tcttgtgggg | tgtctccagc | agtgaggaag | tcgtcaaggc | cattttggga g | agataaag 780 |
| ctttgaagtt | tttcagcatc | actggtcaaa | caatggagag | ttttgtgaag t | cgttagacg 840 |
| gtgatgtcca | ggagctggat | tcggatgaaa | gtcagtttgt | tttcgctctg g | ctggaattg 900 |
| tcacgaatgt | tgctgctata | gcatgtggtc | gtgaattctt | ggttaattca a | gccgggtgc 960 |
| tcttggacac | catattgcag | cttctgggag | acttgaagcc | aggacagtgt a | ccaaactca 1020 |
| aagtgctaat | gctgatgtcc | ctatacaatg | taagcatcaa | tttgaaaggc t | tgaaataca 1080 |
| tcagcgagag | tccaggattc | atccctttgc | tgtggtggct | tttgagtgat c | cagatgcag 1140 |
| aggtgtgcct | tcatgtactg | aggcttgtcc | agtctgtggt | tctggaacct g | aagtcttct 1200 |
| ccaagtcggc | ctctgagttc | cggagctccc | tgccctgca | acgcatcctg g | caatgtcca 1260 |
| agagccgcaa | ccccgcctg | caaaccgcag | cccaggagct | cctggaagat c | tccgcactc 1320 |
| tggagcataa | tgtgtaggtg | tgctcggcca | ccagggtttt | ggtgaaaatg c | cggtgtccc 1380 |
| ttctccccag | atccctcatt | tgatactcca | aaaccatcac | catgtaccat g | tgttagagt 1440 |
| tggcaaaatg | tgattgacta | gagatggaca | tgaattgata | tgtatcccac a | taactttgt 1500 |
| cttggaagtg | agagtgcttg | taggtggttg | gttaagcttg | ccaaaggaga g | gccatgaaa 1560 |
| gaacctgtcc | ttctggaaaa | gtggtccatg | tctgtgctgg | ctggaagagg g | cttgcttag 1620 |
| ggcagcttct | tgctgctcag | cagaccatga | cctgtaggtt | cacctataaa a | cagggaaat 1680 |
| tgaataacca | tctaccccat | tagtcagcat | tttcttgaga | tacatttctt t | gaaaagcaa 1740 |
| ttcattctct | ctctagtaat | tgtaattaat | ccccccaaaa | tgcaagttta c | ttttataac 1800 |
| cttttggtga | acctgctatt | tcggatgaca | ttgggcattt | tagttctata t | tttttgtgc 1860 |
| ctcttttatt | tttgaataaa | gaaatcaga | agagttgtaa | aaaaaaaaaa a | aaaaa 1916 |

HEAT SHOCK TRANSCRIPTION FACTOR-BINDING PROTEIN

This application is the national phase under 35 U.S.C. § 371 of PCT International Application No. PCT/JP98/05728 which has an International filing date of Dec. 18, 1998, which designated the United States of America.

TECHNICAL FIELD

The present invention relates to a heat shock transcription factor binding protein. More particularly, the present invention relates to a DNA encoding a protein possessing a heat shock transcription factor 2 binding activity; a protein encoded by the DNA; an expression vector carrying the DNA; a transformant harboring the expression vector; a process for preparing the protein; an antibody against the protein; an antisense DNA or antisense RNA complementary to the DNA; and an oligonucleotide probe or primer capable of specifically hybridizing to the DNA.

BACKGROUND ART

Heat shock transcription factors (heat shock factor: HSF) bind to the heat shock element (HSE) located upstream of the promoter for heat shock protein (HSP) genes in response to various stresses, thereby regulating the transcription from the promoter.

In HSF of higher eukaryotes, there have been so far known four kinds, namely HSF1, HSF2, HSF3 and HSF4. Among them, HSF1 and HSF3 are activated by stresses including heat, heavy metals and amino acid analogues. HSF2 does not respond to these stresses but is thought to play an important role during differentiation and development. In addition, HSF4 does not have any transcriptional activation domain, and is believed to negatively regulate DNA binding of other HSFs.

The DNA binding activity of HSF2 has been observed in hemin-treated human K562 erythroleukemia cells, in spermatids of mouse testis, in mouse F9 embryonal carcinoma cells, and during early embryogenesis in mice. While the mechanism of the transcriptional regulation of HSP genes by HSF1 has been studied extensively and well understood, very little is known about the transcriptional regulation by HSF2. Concretely, there have been reported that in hemin-treated K562 cells, HSF2 binds to HSE on the HSP70 gene (Sistonen, L. et al., (1992) *Mol. Cell. Biol.* 12, 4104–4144), and that in mouse spermatogenic cells, HSF2 binds constitutively to HSE on the testis-specific HSP70.2 gene (Sarge, K. D. et al., (1994) *Biol. Reprod.* 50, 1334–1343). In each case, HSF2 is deduced to be involved in expression of HSP70 and HSP70.2. On the other hand, in F9 cells, the binding of HSF2 to HSE located upstream of the HSP70 promoter has not been found Murphy, S. P. et al., (1994) *Mol. Cell. Biol.* 14, 5309–5317), and moreover in mouse embryos, no correlation in the expression patterns of the main HSP and HSF2 has been found (Rallu, M. et al., (1997) *Proc. Natl. Acad. Sci. USA* 94, 2392–2397).

Since HSF2 can actually bind to HSE located upstream of the HSP70 promoter in K562 cells or in spermatogenic cells, it is believed that there is a possibility that there exists a factor which regulates activation of HSF2 in these cells. However, the regulatory factor has not yet been known at present.

The term "spermatogenesis" refers to a process in which spermatogonia, immature masculine reproductive cells, proliferate by mitosis to form spermatocytes; meiosis of the spermatocytes takes place to form spermatoblasts; and further complicated morphological changes result in maturing to sperm. During the spermatogenesis process, expression of HSP is strictly regulated. In general, when exposed to deleterious environmental conditions for cells (under stress), such as high temperature, HSP is rapidly induced in order to prevent irreversible denaturation of intracellular proteins and to protect the cells from disorder caused by the stress. Besides the HSP induced by the stress, there are HSPs (i.e. molecular chaperone) having a role of aiding in folding, association and intracellular translocation of nascent proteins even under usual conditions, and these proteins are constitutively expressed in cells. In the process of spermatogenesis, the gene expression of reproductive cells greatly changes, and as a result, intracellular proteins dramatically change. Therefore, HSPs required for folding and localization of these proteins have been regulated so as to be correctly expressed at the necessary timing (Sarge, K. D. and Cullen, K. E., (1997) *Cell. Mol. Life Sci.* 53, 191–197).

Many of HSPs have been identified also in testis as in other tissues and cells. The HSP which is expressed at the highest level in mouse testis is HSP70.2, belonging to the HSP70 family, and its expression is testis-specific and constitutive, and is not induced by heat shock. There have been reported that HSP70.2 is expressed at a high level in meiosis phase of the spermatogenetic process, namely from spermatocytes to spermatoblasts (Allen et al., (1988) *Mol. Cell. Biol.* 8, 828–831; Zakeri, Z. F. et al., (1988) *Mol. Cell. Biol.* 8, 2925–2932), and that meiosis does not take place in mice of which HSP70.2 gene is disrupted, and consequently the spermatoblast is not formed, resulting in infertility (Dix, D. J. et al., (1996) *Proc. Natl. Acad. Sci. USA* 93, 3264–3268). On the other hand, HSF2 is expressed from spermatocytes to spermatoblasts in the spermatogenetic process, and can bind to the HSP70.2 promoter in vitro. Therefore, it is suggested that HSF2 is involved in the transcriptional regulation of HSP70.2 which has a role essential in the spermatogenesis as a molecular chaperone (Sarge, K. D. et al., (1994) *Biol. Reprod.* 50, 1334–1343).

DISCLOSURE OF INVENTION

The present invention has been accomplished in view of the above prior arts, and an object of the present invention is to provide an HSF2 binding factor as an activation regulatory factor of HSF2, which is thought to be involved in the transcriptional regulation of HSP70.2, which has a role essential for spermatogenesis by testis-specific expression. Another object of the present invention is to provide a DNA encoding the HSF2 binding factor. A still another object of the present invention is to provide an expression vector carrying the above DNA or a part thereof, and a transformant harboring the expression vector. A still another object of the present invention is to provide a process for preparing a recombinant protein, comprising culturing the above transformant. A still another object of the present invention is to provide an antibody or a fragment thereof capable of specifically binding to the regulatory factor. A still another object of the present invention is to provide an antisense DNA or antisense RNA of which sequence is complementary to the above DNA. A still another object of the present invention is to provide an oligonucleotide probe or primer capable of specifically hybridizing to the above DNA.

Concretely, the gist of the present invention relates to:

[1] a DNA encoding a protein having a heat shock transcription factor (HSF) 2 binding activity, which is selected from the group consisting of:

(a) a DNA encoding a peptide comprising the amino acid sequence of SEQ ID NO: 1;

(b) a DNA encoding a peptide comprising an amino acid sequence resulting from deletion, substitution, insertion or addition of one or more amino acids in the amino acid sequence of SEQ ID NO: 1;

(c) a DNA comprising the nucleotide sequence of SEQ ID NO: 2;

(d) a DNA comprising a nucleotide sequence resulting from deletion, substitution, insertion or addition of one or more bases in the nucleotide sequence of SEQ ID NO: 2;

(e) a DNA capable of hybridizing with a DNA of any one of (a) to (d), under stringent conditions;

[2] a protein encoded by the DNA of item [1] above;

[3] an expression vector carrying all or a part of the DNA of item [1] above;

[4] a transformant harboring the expression vector of item [3] above;

[5] a process for preparing a recombinant HSF2 binding protein, comprising the step of culturing the transformant of item [4] above under conditions capable of expressing a protein from the expression vector of item [3] above;

[6] an antibody or a fragment thereof capable of specifically binding to the protein of item [2] above;

[7] an antisense DNA or antisense RNA comprising 8 or more bases, of which sequence is complementary to the DNA of item [1] above; and

[8] an oligonucleotide probe or primer, capable of specifically hybridizing to the DNA of item [1] above.

BRIEF DESCRIPTION OF THE DRAWINGS

FIG. 2 is an electrophoretic diagram of a Western blot analysis of a GAL4-BD-HSF2 fusion protein expressed in yeast.

FIG. 3 shows a cDNA sequence (SEQ ID NO:2) of HSF2BP and the corresponding amino acid sequence (SEQ ID NO: 1). The amino acids marked by asterisks or open rectangles are hydrophobic amino acids repeated every heptad residues.

FIG. 5 is an electrophoretic diagram of a Northern blot analysis of mRNAs derived from various tissues, using HSF2BP, HSF2, and G3PDH cDNA each labeled with $^{32}$P as probes. The numbers on the left margin of each panel show the positions of the size markers (units: kb).

FIG. 6 is an electrophoretic diagram showing the in vitro interaction of HSF2BP with HSF2 or HSF1 by GST-pull-down assay. The numbers at the bottom of the panel show the proportion of bound HSF2BP (% to the input).

FIG. 7 is a schematic view showing an HSF2BP protein and deletion mutants thereof The dotted portions show a region having an α-helix structure, and the solid portions show a region of leucine zipper motif.

FIG. 10 is a graph showing the induction fold of the activity obtained by pVPBP as compared to the activity obtained by pVP16 for each HSF by determining the luciferase activities in the two-hybrid assay in K562 cells. The ordinate is expressed as the mean ±SD from four independent experiments.

BEST MODE FOR CARRYING OUT THE INVENTION

Figure 1:
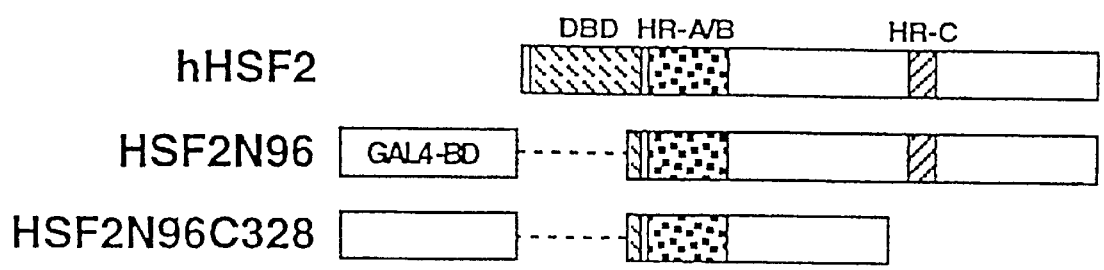
FIG. 1 is a schematic view showing a GAL4-BD-HSF2 fusion protein, used as a bait for two-hybrid screening, and a human HSF2 protein. In the figure, DBD stands for a DNA binding domain; HR-A/B stands for a hydrophobic repeat for trimer formation; and HR-C stands for a C-terminal hydrophobic repeat for negative regulation.

In the present invention, the term "eat shock transcription factor (HSF) 2" refers to HSF2 derived from higher eukaryotes, including human and mammals, and HSF2 derived from human is preferable. The human HSF2, as shown in FIG. 1, has a structure comprising a DNA binding domain (DBD); a hydrophobic repeat for trimer formation (HR-A/B); and a C-terminal hydrophobic repeat for negative regulation (HR-C).

The protein having HSF2 binding activity of the present invention may be capable of binding to any regions of HSF2. From the viewpoint of regulating the activation of HSF2 involved in the transcriptional regulation of HSP70.2, it is preferable that the protein is capable of binding to any of regions of transcriptional activation region, transcriptional activation suppression region, and trimerization region of HSF2.

The term "protein having an HSF2 binding activity (hereinafter abbreviated in some cases as 'HSF2 binding protein' or 'HSF2BP')" of the present invention refers to a protein encoded by the DNA of the present invention which is described below. Concretely, the protein includes a peptide comprising the amino acid sequence of SEQ ID NO: 1, and this protein is a testis-specifically expressed protein having a molecular weight of about 38 kD, the protein having 334 amino acid residues, which is named human HSF2BP.

The binding activity of HSF2BP of the present invention to HSF2 can be determined in vitro or in vivo by glutathione S-transferase (GST) pull-down assay described in Example 4 given below, or by two-hybrid assay described in Example 5, respectively.

The DNA of the present invention is a DNA encoding a protein having a heat shock transcription factor (HSF) 2 binding activity, which is selected from the group consisting of (a) a DNA encoding a peptide comprising the amino acid sequence of SEQ ID NO: 1;

(b) a DNA encoding a peptide comprising an amino acid sequence resulting from deletion, substitution, insertion or addition of one or more amino acids in the amino acid sequence of SEQ ID NO: 1;

(c) a DNA comprising the nucleotide sequence of SEQ ID NO: 2;

(d) a DNA comprising a nucleotide sequence resulting from deletion, substitution, insertion or addition of one or more bases in the nucleotide sequence of SEQ ID NO: 2;

(e) a DNA capable of hybridizing with a DNA of any one of (a) to (d) mentioned above, under stringent conditions.

The DNA of the present invention is concretely a DNA encoding a peptide comprising the amino acid sequence of SEQ ID NO: 1, and more concretely a DNA comprising the nucleotide sequence of SEQ ID NO: 2, which is human HSF2BP gene.

The DNA of the present invention also encompasses a DNA encoding a peptide comprising an amino acid sequence resulting from deletion, substitution, insertion or addition of one or more amino acids in the amino acid sequence of SEQ ID NO: 1, as long as the peptide has an HSF2 binding activity. The term "one or more" in the present specification means a number of one or several or more.

In addition, the DNA of the present invention also encompasses a DNA comprising a nucleotide sequence resulting from deletion, substitution, insertion or addition of one or more bases in the nucleotide sequence of SEQ ID NO: 2, as long as the peptide encoded by the DNA has an HSF2 binding activity. Here, the term "one or more" has the same meaning as described above.

The techniques for deletion, substitution, insertion or addition of amino acids and bases mentioned above can be readily performed by one of ordinary skill in the art by site-directed mutagenesis, PCR method, or the like as described in, for instance, Sambrook, J. et al., *Molecular Cloning: A Laboratory Manual*, 2nd edition, Cold Spring Harbor Laboratory Press, New York, published in 1989.

Further, the DNA of the present invention also encompasses a DNA capable of hybridizing with a DNA according to any one of (a) to (d) mentioned above, under stringent conditions, as long as the peptide encoded by the DNA has an HSF2BP binding activity.

In the present specification, the term "capable of hybridizing under stringent conditions" refers to a state in which positive hybridization signals are still observed even under the conditions, for instance, of heating at 42° C. in a solution containing 6×SSC (20×SSC refers to 333 mM sodium citrate and 333 mM NaCl), 0.5% SDS and 50% formamide, and thereafter washing at 68° C. in a solution containing 0.1× SSC and 0.5% SDS.

From the viewpoint of screening a DNA encoding a protein having an HSF2 binding activity, the DNA of the present invention is isolated from human testis cDNA library by yeast two-hybrid screening method using GAL4-BD (GAL4 DNA binding domain)-HSF2 fusion protein as a bait. The details of the yeast-two hybrid screening method [Fields, S. and Song, O.-K., (1989) *Nature* 340, 245–246; Fields S. and Sternglanz, R., (1994) *Tends Genetics* 10, 286–292; Mendelsohn, A. R. and Brent, R., (1994) *Curr. Opin. Biotechnol.* 5, 482–486] are described in Example 1 given below.

When a bait to be used for the yeast two-hybrid screening method mentioned above is prepared, it is important to consider the following features for the success in the screening of the DNA of the present invention. In other words, HSF2 per se is a transcription activation factor, and in order to eliminate the possibility of interference by the transcriptional activity of the HSF2 per se, a vector for expressing a fusion protein of the GAL4-BD mentioned above and HSF2 deletion mutant is prepared by constructing HSF2 deletion mutant in which the DNA binding domain (DBD) of HSF2 is removed, or the DBD and transcriptional activation domain (C-terminal side from HR-C) are removed.

As a vector for a bait, those commercially available can be suitably utilized. For the expression of fusion protein with GAL4-BD, the vector includes, for instance, pGBT9 (Clontech), HybriZAPII (Stratagene), and the like.

As an yeast strain usable for the yeast two-hybrid screening method, those commercially available can be suitably utilized. The yeast strain includes, for instance, *Saccharomyces cerevisiae* strain HF7c (MATα, ura3-52, his3-200, lys2-801, trp1-901, ade2-101, leu2-3,112, gal4-542, gal80-538, LYS::GAL1-HIS3, URA3::(GAL4 17 mers)3-CYC1-lacZ); and *Saccharomyces cerevisiae* strain CG1945 (MATα, ura3-52, his3-200, lys2-801, trp1-901, ade2-101, leu2-3,112, gal4-542, gal80-538, LYS::GAL1-HIS3, cyhr2, URA3::(GAL4 17 mers)3-CYC1-lacZ) (both available from Clontech), and the like. The yeast strain mentioned above carries two reporter genes (HIS3 and lacZ), which can be expressed under the control of GAL4-responsive elements, on the chromosomes.

The number of His$^+$ and βGal$^+$ transformants is tested in the manner described in item (4) of Example 1 given below using pGBT9 as a vector for a bait and strain HF7c as an yeast strain. In the present invention, fusion proteins of GAL4-BD with HSF2N96 (having amino acid residue 96 to C-terminal) deletion mutant and HSF2N96C328 (having amino acid residues 96 to 328) deletion mutant, respectively, are used as baits, wherein HSF2N96 is thought to be able to fish out a molecule interacting with DNA-binding and transcriptionally inactive form of HSF2, and wherein HSF2N96C328 is appropriate for isolating other molecules interacting with the active form of HSF2. These schematic views are shown in FIG. 1.

The expression vector of the present invention carries all or a part of the DNA mentioned above. The expression vector usable in the present invention includes, for instance, commercially available expression vectors and known expression vectors, such as pKK223, pET, pGEX, pBacPAK, pcDL-SRα, and pCAGGS, and the expression vector is not particularly limited, as long as the DNA of the present invention can be inserted thereto, and expressed therefrom.

As a method for inserting the DNA of the present invention to a vector, there can be employed a method as described in *Molecular Cloning*, mentioned above, and the like.

The transformant of the present invention is obtainable by introducing the above expression vector into a desired host cell. The host cell may be any of prokaryotic cells such as *Escherichia coli*, or eukaryotic cells such as yeasts, animal cells and insect cells, which is selected depending upon the expression vector used.

As a method for introducing an expression vector, a known method, including, for instance, calcium phosphate method, lipofection method, DEAE dextran method, electroporation method [edited by Ausubel, F. M. et al., *Current Protocols in Molecular Biology*, John Wiley and Sons, Inc. (1987)], or the like may be employed.

The present invention provides a process for preparing a recombinant HSF2BP comprising the step of culturing under conditions capable of expressing the protein of the present invention from the above expression vector. An embodiment where *E. coli* is selected as a host cell and pGEX5X-1 is used as an expression vector is hereinafter described.

In order to express as a fusion protein of HSF2BP with GST in *E. coli*, GST-HSF2BP expression plasmid is prepared by inserting HSF2BP cDNA to an expression plasmid pGEX5X-1. Thereafter, *E. coli* is transformed with the expression plasmid, and the transformed cells are cultured under usual conditions. Subsequently, isopropyl-β-D-thiogalactoside (IPTG) is added to the resulting culture, thereby inducing expression of GST-HSF2BP fusion protein. The fusion protein can be recovered mainly as an insoluble fraction in the cell disruption solution, and further purified by separating on SDS-PAGE.

In addition, the prepared recombinant HSF2BP can be readily purified by such a method as usual column chromatography or affinity purification using the antibody of the present invention.

Further, the present invention provides an antibody or a fragment thereof capable of specifically binding to the protein of the present invention. The antibody may be a polyclonal antibody or monoclonal antibody, or it may be a chimeric antibody.

The antibody of the present invention can be readily prepared by appropriately immunizing an animal using all or a part of the protein of the present invention in accordance with the method described in, for instance *Antibodies: A Laboratory Manual*, edited by Lane, H. D. et al., Cold Spring Harbor Laboratory Press, New York, published in 1989, or the like, thereby giving an antibody capable of specifically binding to the protein of the present invention or an antibody neutralizing an activity of the protein. In addition, an antibody fragment can be prepared by cleaving the resulting antibody with a protease, or the like.

The application of the antibody or fragment thereof includes affinity chromatography, screening of cDNA library, immunological diagnostic method, pharmaceuticals, and the like. The immunological diagnostic method can be appropriately selected from immunoblotting method, radioimmunoassay (RIA), enzyme immunoassay (ELISA), fluorescence or luminescence assay, or the like.

The present invention provides an antisense DNA or antisense RNA comprising 8 or more bases, of which sequence is complementary to the DNA of the present invention. The antisense DNA or antisense RNA can be obtained by artificial synthesis using a synthesizer, by transcription of a DNA in a direction opposite from the usual direction (namely antisense direction), or the like.

The above antisense DNA or antisense RNA may be introduced into a cell, whereby the expression of the protein of the present invention can be suppressed. In view of the above, the length of the antisense DNA or antisense RNA is usually 8 to 2000 bases, preferably 15 to 1916 bases. mRNA produced by transcription of a usual gene is a sense strand, and the antisense DNA or antisense RNA binds to the sense strand mRNA intracellularly, so that the translation from the mRNA is suppressed, thereby regulating the production of HSF2BP, the protein of the present invention. By having the above action, the antisense DNA or antisense RNA is used, for instance, as a regulating agent for HSF2 activity, and is expected to have regulatory action of the spermatogenesis. In addition, the antisense DNA or antisense RNA can be utilized as a research reagent for in situ hybridization, or the like.

Whether or not the prepared antisense DNA or antisense RNA has the desired suppression effects can be readily found from, for instance, the following two methods. One is a method of directly introducing an antisense DNA or anfisense RNA from outside of the cells to the cells expressing the HSF2BP of the present invention, and thereafter using a change in the expression level of the HSF2BP as an index; and another is a method of introducing a vector capable of producing the antisense RNA by transcription into the above HSF2BP expressing cells, and thereafter using a change in the expression level of the HSF2BP as an index.

The present invention provides an oligonucleotide probe or primer, capable of specifically hybridizing to the DNA of the present invention. The length of the oligonucleotide probe or primer can be selected in accordance with its purpose. The length of the oligonucleotide probe is usually 8 to 2000 bases, preferably 15 to 1916 bases, and the length of the oligonucleotide primer is usually 8 to 50 bases, preferably 15 to 30 bases. The oligonucleotide probe or primer can be usually prepared by chemical synthesis using a synthesizer, or enzymatic synthesis using DNA polymerase I (Klenow fragment), or PCR method.

The hybridization conditions for the oligonucleotide probe or primer of the present invention can be easily set depending upon the purposes in accordance with the method as described in, for instance, Sambrook, J. et al., *Molecular Cloning: A Laboratory Manual*, 2nd edition, Cold Spring Harbor Laboratory Press, New York, published in 1989.

The oligonucleotide probe or primer of the present invention is used for detection and quantitation of HSF2BP, and expected to be useful in diagnosis or treatment in the spermatogenesis. In addition, the probe or primer can be also utilized as a research reagent for dysspermatogenesis usable for hybridization, PCR, or the like.

EXAMPLES

The present invention will be described in further detail by means of the following working examples, but the present invention is by no means limited to these working examples. Unless specified otherwise, the following examples were carried out by methods described in Sambrook, J. et al., *Molecular Cloning: A Laboratory Manual*, 2nd edition, Cold Spring Harbor Laboratory Press, New York, published in 1989; *Current Protocols in Protein Science* (edited by Coligan, J. E. et al.), John Wiley and Sons, Inc., and the like.

Example 1

Two-Hybrid Screening Method (1) Construction of Plasmid

The plasmid phHSF2-1 carrying human HSF2 cDNA was provided by Dr. R. E. Kingston. A human HSF1 cDNA was obtained by RT-PCR method using human brain mRNA (Clontech) as a template, and subcloned into the EcoRI site of pBluescript II (Stratagene). The resulting construct was named phHSF1. The phHSF1 carries nucleotides from −21 to +1704 of the cDNA sequence for human HSF1.

(2) Construction of Bait

In order to screen proteins interacting with HSF2 by yeast two-hybrid screening method, HSF2 deletion mutants were constructed by removing the DNA binding domain and/or the transcriptional activation domain of HSF2 from the above phHSF2-1, thereby removing the possibility of interfering by the transcriptional activity of HSF2 per se. Concretely, phHSF2-1 DNA was cleaved with appropriate restriction enzymes, blunted, if necessary, by Klenow fragment or T4 DNA polymerase, and ligated either with an NcoI linker (8 mer, 10 mer or 12 mer) for N-terminal deletion or with a linker containing multiple termination codons for C-terminal deletion. These DNA fragments were inserted into the multiple cloning site of pAS2. In addition, as a control, HSF1 deletion mutants were constructed in the same manner from the phHSF1 mentioned above.

As a bait for yeast two-hybrid screening method, pAS2 or pGBT9 (Clontech), each carrying a sequence encoding GAL4 DNA binding domain (GAL4-BD), was fused with a cDNA of the deletion mutant of HSF2 or HSF1 mentioned above, so that both of the open reading frames matched each other.

In the present invention, as described in item (4) of Example 1 described below, deletion mutant of HSF2N96

(having amino acid residue 96 to C-terminal) or HSF2N96C328 (having amino acid residues 96 to 328) was used as a bait. Schematic views thereof are shown in FIG. 1.
(3) Confirmation of Expression of HSF2 Deletion Mutants in Yeast by Western Blotting Yeast cells CG1945 were transformed by the lithium-acetate method with the fusion expression plasmid obtained in item (2) above, the expression plasmid for fusion protein of GAL4-BD from pGBT9 with HSF2 deletion mutant of the above HSF2N96 or HSF2N96C328. Each of the proteins was extracted from the transformed cells by conventional method using glass beads. The concentration of the resulting protein was determined by a Bio-Rad protein assay kit (Bio-Rad). The cell extract (20 μg protein) was separated on 8% SDS-PAGE. After subjecting to electrophoresis, each of proteins was elecroblotted onto nitrocellulose membrane filter (Amersham). The filter was blocked at room temperature for 1 hour with 5% skim milk in PBS containing 0.1% Tween 20 (PBST), and incubated at room temperature for 1 hour with 1:2000 dilution of polyclonal rabbit antibodies against chicken HSF2 (αHSF2α, provided by Dr. Akira Nakai) in PBST containing 2% skim milk. After washing with PBST, the filter was incubated at room temperature for 1 hour with 1:2000 dilution of horseradish peroxidase-conjugated goat F(ab')$_2$ anti-rabbit antibody (Biosource). After washing with PBST, signals were detected using ECL reagent (Amersham) (FIG. 2).

It was found from FIG. 2 that these HSF2 deletion mutants were expressed in the yeast cells as fusion proteins with GAL4-BD.

(4) Screening of Human Testis cDNA Library by Two-Hybrid Method

*Saccharomyces cerevisiae* strain HF7c and a cDNA library derived from human testis constructed with pGAD10 carrying a sequence encoding GAL4 activator (GAL4-AD), which were used for two-hybrid screening method, were purchased from Clontech. The strain HF7c carries two reporter genes HIS3 and lacZ, capable of being expressed under the control of GAL4-responsive elements, on the chromosomes.

HF7c expressing the HSF2 deletion mutant obtained in item (3) above was transformed by the lithium-acetate method with a plasmid of the above cDNA library derived from human testis. The transformants were spread on Leu⁻, Trp⁻ and His⁻ plates containing 10 mM 3-aminotriazole to select for His⁺ cells. Subsequently, the His⁺ transformant cells were tested for expression of the second reporter lacZ by the filter assay for β-galactosidase (βGal) activity. From βGal positive colonies, plasmid DNAs were isolated, and a nucleotide sequence for the 5' end of each cDNA insert was determined by using a DNA autosequencer PRISM 377 (Perkin Elmer).

TABLE 1

Results of Two-Hybrid Screening

| HSF2 Bait | Number of Screened Clones | His⁺ | βGal⁺ | Number of Sequenced Clones | HSF2BP |
|---|---|---|---|---|---|
| N96C328 | 4.98 × 10⁷ | 14 | 9 | 9 | 2 |
| N96 | 6.80 × 10⁷ | 1487 | 786 | 93 | 39 |

As shown in Table 1, when HSF2N96 was used as a bait, 786 His⁺ and βGal⁺ clones were obtained from 6.80×10⁷ transformants. On the other hand, when HSF2N96C328 was used as a bait, only 9 His⁺ and βGal⁺ clones were obtained from 4.98×10⁷ transformants. From the above findings, it is considered that most of the above 786 clones are true positive.

Nucleotide sequences near the 5' end of 93 clones randomly selected from the above 786 clones and of all the above 9 clones were determined. With focusing on a unique cDNA sequence that was found most abundantly, i.e. 39 out of 93 to the bait of HSF2N96, and 2 out of 9 to the bait of HSF2N96C328, the following cloning was carried out.

Example 2

Cloning of Full-Length cDNA for HSF2BP

In order to isolate a full length cDNA clone, a human testis cDNA library (λgt11 containing 1×10⁶ independent clones, Clontech) was screened by plaque hybridization using the cDNA fragment obtained in item (4) of Example 1 as a $^{32}$P-labeled probe. The longest clone was subcloned into pBluescriptII (Stratagene), and its nucleotide sequence was determined.

Figure 3:
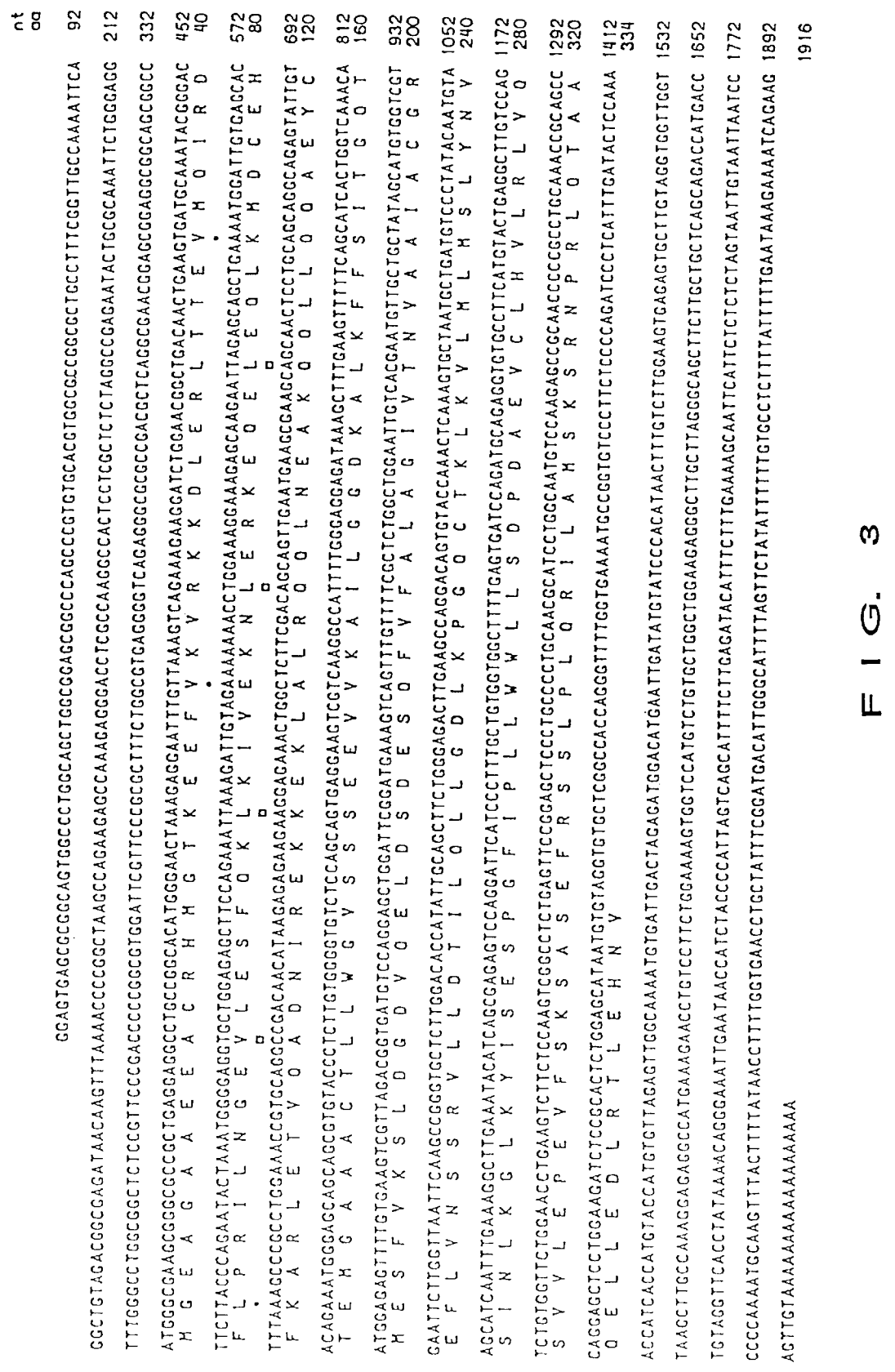
Figure 4:
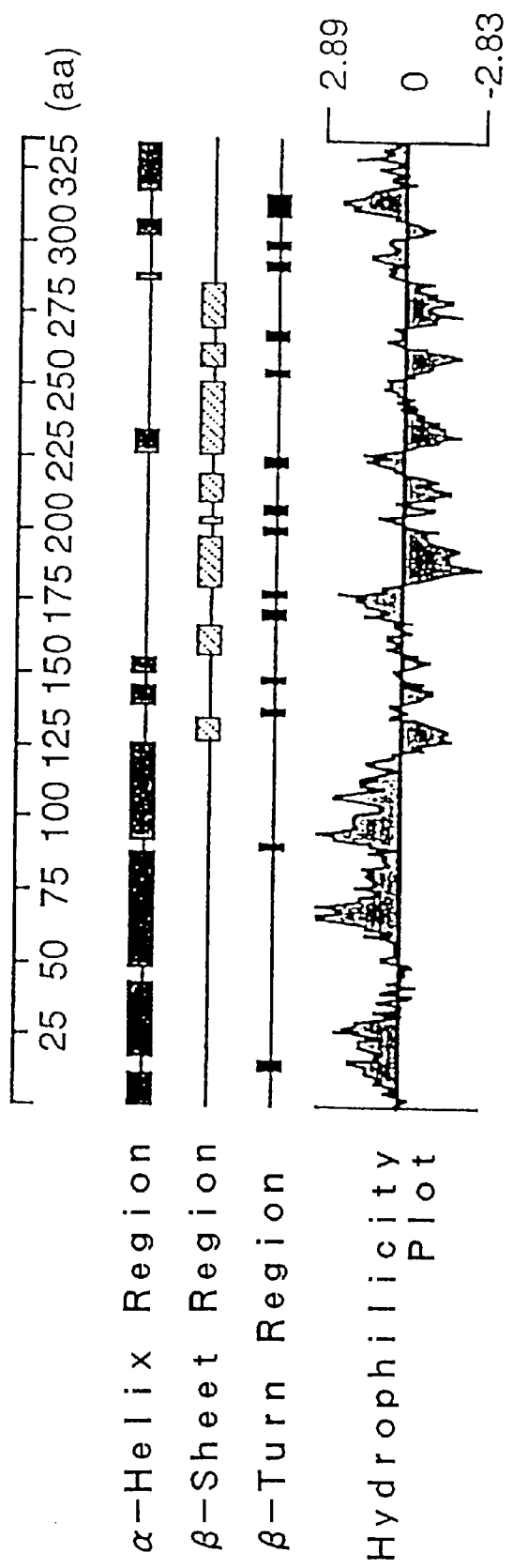
FIG. 4 shows α-helix, β-sheet and β-turn regions of HSF2BP as predicted by Chou-Fasman method, and a hydrophilicity plot as predicted by Kyte-Doolittle method.

The resulting longest cDNA clone had a length of 1916 bp, and contained an open reading frame encoding 334 amino acids (molecular weight 37,644 Daltons), comprising a hydrophilic amino terminal region and a hydrophobic carboxyl terminal region. The protein encoding this cDNA was named HSF2 binding protein (HSF2BP) (FIG. 3). The amino 5 terminal half was deduced to constitute an α-helix structure, and to contain two leucine zipper motifs (FIG. 4).

Example 3

Northern Blot Analysis

RNA blots of multiple human tissues (MTN blot and MTNII blot) purchased from Clontech were hybridized overnight at 42° C. with $^{32}$P-labeled cDNA probes for HSF2BP, HSF2, and glyceraldehydes 3-phosphate dehydrogenase (G3PDH, Clontech) in 5×SSPE/50% formamide/5× Denhardt's solution/0.1% SDS, washed twice with 0.1× SSPE containing 0.1% SDS at 42° C. for 30 minutes, and thereafter subjected to audiography (FIG. 5).

As shown in FIG. 5, it is found that the HSF2BP mRNA is approximately 1.7 kb long, which is testis-specifically expressed. HSF2 is also specifically expressed in testis at a high level as reported elsewhere. Because the constitutive binding of HSF2 to HSE is observed in mouse testis and correlated with the testis-specific expression of HSP70.2 (Sarge, K. D. et al., *Biol. Reprod.* 50 (1994) 1334–1343), there is suggested a possibility that HSF2BP serves to testis-specifically regulate expression of HSP70.2 by the interaction with HSF2.

Example 4

GST Pull-Down Assay (1) Construction of Plasmid

For glutathione S-transferase (GST) pull-down assay, GST fusion construct for deletion mutant of HSF2 or HSF1 was prepared using a pGEX-5X-1 vector (Pharmacia). The GST protein, the fusion protein of GST-HSF2 deletion mutant, and the fusion protein of GST-HSF1 deletion mutant were expressed in *E. coli*.

For in vitro translation of HSF2BP and its deletion mutants, in accordance with the method described in item (1) of Example 1, each expression plasmid resulting from insertion of the corresponding region of HSF2BP cDNA into pcDNA 3.1 His A, pcDNA 3.1 His B or pcDNA 3.1 His C (Invitrogen) was prepared.

(2) In vitro Translation of HSF2BP and GST Pull-Down Assay

Each of the GST protein and the fusion protein of the GST-HSF2 deletion mutant as expressed in item (1) above was purified with glutathione-Sepharose (Pharmacia), and immobilized on the glutathione-Sepharose in accordance with the instruction of the manufacturer, to prepare GST-Sepharose and various GST-HSF2 Sepharoses. As a control, each of the fusion proteins of the GST-HSF1 deletion mutants was purified, and various GST-HSF1 Sepharoses were prepared in the same manner. In vitro translation was carried out with expression plasmids of HSF2BP and its deletion mutants described in item (1) of Example 4 as templates by using a TNT translation kit (Promega) in accordance with the instruction of the manufacturer, to give in vitro translation products of HSF2BP and its deletion mutants labeled with $^{35}$S-methionine.

Five microliters of each of the resulting in vitro translation products was incubated overnight at 4° C. with the above GST-Sepharose and various kinds of Sepharoses of the fusion proteins of the GST-HSF2 deletion mutants. The Sepharose beads were washed with NETN buffer (20 mM Tris-HCl, pH 8.0, 100 mM NaCl, 1 mM EDTA, 0.5% Nonidet P-40), and binding proteins were analyzed by SDS-PAGE, processed to be subjected to autoradiography, and quantified by an imaging analyzer BAS2000 (Fuji) (FIG. 6).

As shown in FIG. 6, the in vitro translated HSF2BP shows significant binding to both GST-HSF2N96 (7.9% of the level of input) and GST-HSF2N96C328 (9.3% of the level of input), whereas the binding to GST-HSF2N199C328 lacking the trimerization domain was of the same level to GST alone (anes 1 to 5). These results suggesting that the interaction is mediated by the trimerization domain of HSF2 are consistent with the results of the two-hybrid screening in the yeast of Example 1.

The interaction of HSF2BP and HSF1 deletion mutants was also examined in the same manner as above, using constructs of the GST-HSF1 deletion mutants resembling to the above three GST-HSF2 deletion mutants (FIG. 6, lanes 6 to 8). GST-HSF1N101 comprises a whole HSF1 except for the DNA binding domain, GST-HSF1N101C318 comprises the trimerization domain and the heat shock-responsive domain, and GST-HSF1N202C318 comprises only the heat shock-responsive domain. HSF2BP bound to GST-HSF1N101 (8.5% of the level of input) (lane 6), but not bound to GST-HSF1N101C318 and GST-HSF1N202C318 (lanes 7 and 8). It is suggested from these results that HSF2BP can also interact with HSF1 in vitro, but the binding profile is different from that observed for HSF2.

(3) In vitro Translation of Deletion Mutants of HSF2BP

In order to determine the region of HSF2BP, interacting with HSF2, four deletion mutants of HSF2BP (BP-C150, BP-C115, BP-C73 and BP-N115) were constructed in accordance with the method described in item (2) of Example 1 (FIG. 7).

Figure 8:
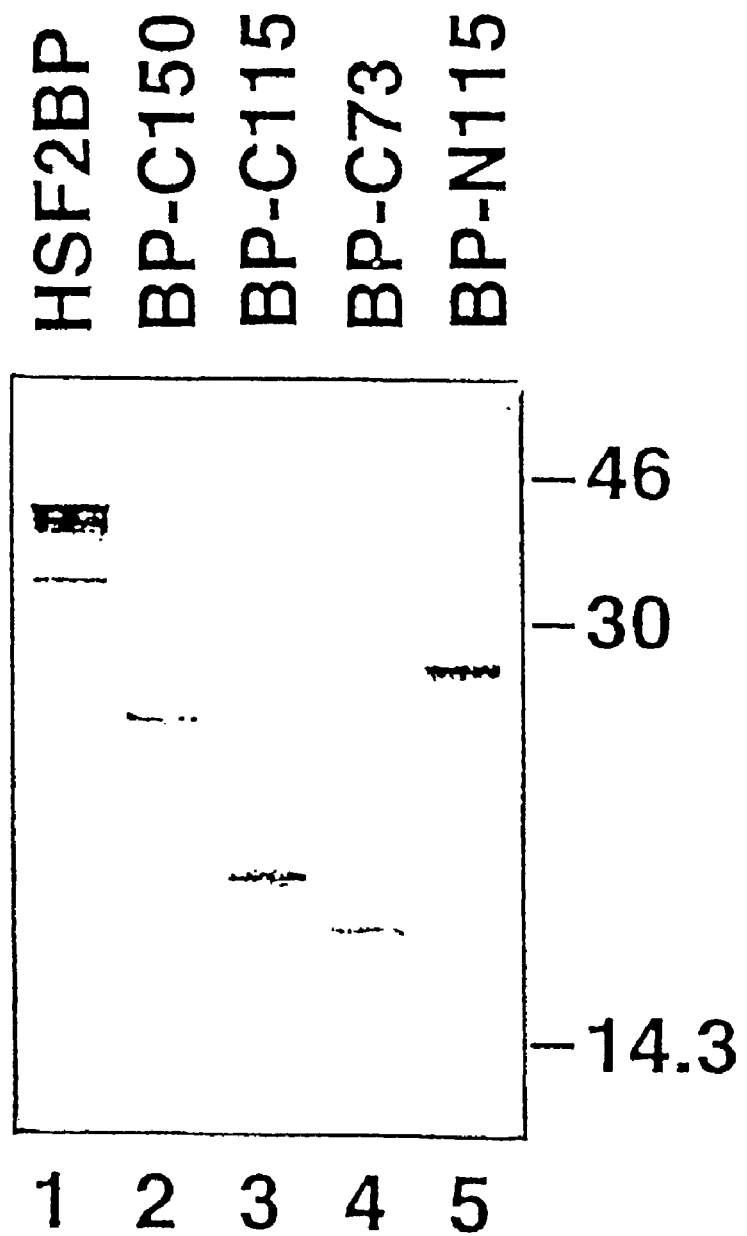
FIG. 8 is an electrophoretic diagram by SDS-PAGE analysis of the HSF2BP protein and deletion mutants thereof shown in FIG. 7 which are in vitro translated using $^{35}$S-methionine. The numbers on the right margin of the panel show size markers (units: kD).
Figure 9:
FIG. 9 is an electrophoretic diagram showing the in vitro interaction of the HSF2BP and deletion mutants thereof shown in FIG. 7 with HSF2N96C328 by GST-pull-down assay. Lanes 1, 4, 7, 10 and 13 show levels of input; lanes 2, 5, 8, 11 and 14 show binding to GST; and lanes 3, 6, 9, 12 and 15 show binding to GST-HSF2N96C328. The numbers of the panel respectively show the proportion of the bound HSF2BP or deletion mutants thereof.

In the same manner as the method in item (2) of Example 4, in vitro translated, $^{35}$S-methionine-labeled HSF2BP deletion mutant protein was confirmed by Western blotting method (FIG. 8), and subjected to pull-down assay with GST-HSF2N96C328 (FIG. 9).

As shown in FIG. 9, as compared with intact HSF2BP (12.9% bound to the level of input), a larger amount of BP-C150 (22.3% bound) and a smaller amount of BP-C115 (5.7% bound) bound to GST-HSF2N96C328 (anes 1 to 9), whereas BP-C73 and BP-N115 did not bind thereto (anes 10 to 15). It is suggested from these results that the N-terminal half of HSF2BP satisfy necessary and sufficient conditions for the interaction with HSF2. The N-terminal α-helix domain of HSF2BP contains two leucine zipper motifs. It is thought that the interaction is mediated between HR-A/B region of HSF2 and the leucine zippers. However, the fact that BP-C73 could not bind to HSF2, while still carrying two leucine zippers, suggests that a region other than the leucine zippers of the α-helical domain is also necessary for the interaction.

Example 5

Two-Hybrid Assay of HSF2 and HSF2BP in Mammalian Cells

In order to examine whether or not HSF2BP interacts with both HSF2 and HSF1 in vivo, two-hybrid assays were performed. K562 cells (ATCC CCL243) (1×10$^6$ cells) cultured at 37° C. in 5% $CO_2$ in RPMI-1640 medium containing 10% fetal bovine serum were transfected by the lipofection method using Transfectam™ (Promega) with the expression plasmids of HSF2 or HSF1 deletion mutant fused with the yeast GAL4-BD derived from pM (Clontech), with the expression plasmid (pVP16BP) of HSF2BP fused with the VP16 transcriptional activation domain derived from pVP16 (Clontech), and with pGLG4E5 reporter plasmid carrying luciferase gene. After incubating at 37° C. for 48 hours in 5% $CO_2$, the transformed K562 cells were washed twice with PBS, and the luciferase activity was assayed by using Dual-Luciferase Reporter Assay System (Promega) in accordance with the instruction of the manufacturer (FIG. 10).

As shown in FIG. 10, the coexpression of GAL4-HSF2N96C238 with VP16-HSF2BP activated the luciferase reporter in about eleven times as much as the coexpression of GAL4-HSF2N96C238 with the control VP16. This fact suggests that HSF2 interacts with HSF2BP in mammalian cultured cells. On the other hand, any significant interactions of HSF2N96 with HSF2BP were not detected on the two-hybrid assay in K562 cells, although many HSF2BP clones were obtained from the yeast two-hybrid screening using HSF2N96 bait. Two kinds of HSF1 deletion mutants also did not interact with HSF2BP.

Example 6

Preparation of Recombinant HSF2BP (1) Construction of Plasmid

In order to express a recombinant HSF2BP as a fusion protein with GST in E. coil, a cDNA fragment carrying a whole coding region of HSF2BP was inserted into NotI site of an expression vector pGEX-5X-1. The resulting expression plasmid for GST-HSF2BP was referred to as "pGEXBP."

(2) Expression and Purification of Fusion Protein

E. coli (DH5α) transformed with pGEXBP was cultured at 27° C. in 2×YT medium containing 2% glucose. When the absorption at 600 nm became about 0.8, IPTG (Gsopropyl-β-D-thiogalactoside) was added thereto, so as to have a final concentration of 0.1 mM, thereby inducing expression of the GST-fusion protein. Further, the cells were cultured for additional 2 hours, and thereafter harvested. The cells were suspended in PBS containing 1% Triton X-100, ultrasonically disrupted, and centrifuged (10000 rpm for 15 minutes, with a high-performance microcentrifugal machine for 1.5 ml tubes), to collect a sediment fraction. The GST-HSF2BP protein formed intracellular inclusion bodies to be collected in the sediment fraction. The resulting fraction was further separated on SDS-PAGE, and the desired protein was eluted from the gel excised, thereby giving almost uniformly purified GST-HSF2BP protein.

INDUSTRIAL APPLICABILITY

The HSF2BP, which is a heat shock transcription factor binding protein of the present invention is a testis-specifically expressed protein, and can be utilized for research, diagnosis and/or treatment of dysspermatogenesis by regulating the activation of HSF2, which has been suggested to be involved in the transcriptional regulation of HSP70.2, which plays an essential role for spermatogenesis as a molecular chaperone. The antisense DNA or antisense RNA of the present invention is used as a regulating agent for the HSF2 activity, and is expected to have the regulation action for the spermatogenesis. In addition, the antisense DNA or antisense RNA can be utilized as a research reagent for in situ hybridization or the like. The oligonucleotide probe or primer capable of specifically hybridizing to a DNA encoding the HSF2BP can be used for detection and quantitation of the HSF2BP. In addition, the antibody for HSF2BP can be used for detection and quantitation of the HSF2BP. Further, the agonist and antagonist for HSF2BP can be screened by using the HSF2BP, and the agonist and antagonist are used as regulating agents for HSF2 activity, and are expected to have the regulation action for the spermatogenesis.

What is claimed is:

1. An isolated DNA encoding a protein having a heat shock transcription factor (HSF) 2 binding activity, which is selected from the group consisting of:
   (a) a DNA encoding a peptide comprising the amino acid sequence of SEQ ID NO:1;
   (b) a DNA comprising the nucleotide sequence of SEQ ID NO:2; and
   (c) a DNA capable of hybridizing with a DNA of any one of (a) to (b), under the following stringent conditions: heating at 42° C. in a solution containing 6×SSC, 0.5% SDS and 50% formamide, followed by washing at 68° C. in a solution containing 0.1×SSC and 0.5% SDS.

2. An isolated protein encoded by the DNA of claim 1.

3. An expression vector comprising all or a part of the DNA of claim 2.

4. An isolated transformed cell comprising the expression vector of claim 3.

5. A process for preparing a recombinant HSF2 binding protein, comprising the step of culturing the transformant of claim 4 in vitro under conditions for expressing the HSF2 binding protein from the expression vector and recovering said expressed recombinant HSF2 binding protein.

6. An isolated antibody or a fragment thereof which specifically binds to the protein of SEQ ID NO:1.

7. An antisense DNA or antisense RNA having a sequence that is complementary to the DNA of SEQ ID NO:2.

* * * * *